(12) United States Patent
Pauly et al.

(10) Patent No.: US 6,403,125 B1
(45) Date of Patent: Jun. 11, 2002

(54) UTILIZATION OF AN EXTRACT OF A PLANT OF THE CECROPIA GENUS

(75) Inventors: Gilles Pauly, Nancy; Christian Moretti, Paris, both of (FR)

(73) Assignee: Cognis France (Societe Anonyme), Saint Martory (FR)

(*) Notice: Subject to any disclaimer, the term of this patent is extended or adjusted under 35 U.S.C. 154(b) by 0 days.

(21) Appl. No.: 09/868,722

(22) PCT Filed: Dec. 16, 1999

(86) PCT No.: PCT/EP99/10031
§ 371 (c)(1),
(2), (4) Date: Jun. 21, 2001

(87) PCT Pub. No.: WO00/37038
PCT Pub. Date: Jun. 29, 2000

(30) Foreign Application Priority Data

Dec. 21, 1998 (FR) .............................. 98 16289

(51) Int. Cl.$^7$ .......................... A61K 35/78; A61K 31/74

(52) U.S. Cl. ...................... 424/769; 424/725; 424/775; 424/774; 424/777; 424/778; 424/78.02; 424/78.03

(58) Field of Search .................. 424/725, 775, 424/774, 777, 778, 489, 78.02, 78.03, 169

(56) References Cited

PUBLICATIONS

Suarez, Acta Biol. Venezuela (1995), vol. 15 (3–4): 41–54. Medicinal use of trees of the Cantaniapo River humid forest, Amazonas State. Venezuela. El uso medicinal de los arboles del bosque humedo del Rio Cataniapo, Estado Amazonas, Venezuela.*

Grenand et al., Pharmacopees traditionnelles en Guyane: Creoles, Palikur, Wayapi, Orstrom, 1987, pp 315–316.*

G. Bulhoes et al., Phytochemical Screening of Plants Native to Northeastern Brazil, *An. Fac. Farm., Univ. Fed. Pernambuco*, 1977 vol. Date 1976, No. 15, pp 39–44, XP–002115142.

J. J. Marshall et al., Characterization of The .Alpha. –d–glucan Fromt Eh Plastids of Cecropid Peltata as a Glycogen–type Poly–saccharaide, *Dep. Bot. Plant Pathol., Oregon State Univ., Carbohyd. Res.*, 1972, vol. 28, No. 1. pp 31–7, XP–002115143.

R. Neidlein et al., Isolation and Structure of Constituents from Cecropia Adenopus Martius Part 1, *Arch. Pharm.* (Weinheim, DE) 1980, vol. 313, No. 3, pp 193–8.

* cited by examiner

*Primary Examiner*—Christopher R. Tate
*Assistant Examiner*—Michele C. Flood
(74) *Attorney, Agent, or Firm*—Young & Thompson

(57) ABSTRACT

The utilization of at least one extract of a plant belonging to the cecropia genus as an active agent. The extract is used alone or in conjunction with at least one other active agent for preparing a cosmetic or dermopharmaceutical product or a cosmetic or dermopharmaceutical composition for external local application on the skin, the mucous membranes and/or the epithelial or body appendage formations.

20 Claims, No Drawings

UTILIZATION OF AN EXTRACT OF A PLANT OF THE CECROPIA GENUS

The present invention relates to the cosmetics field, particularly dermo-cosmetics, with the object of using at least one extract of a plant of the Cecropia genus in cosmetics, and of using a cosmetic or dermo-pharmaceutical product which contains at least one such extract.

BACKGROUND OF THE INVENTION

The Cecropia genus (MORACEAE) includes approximately 100 quick-growing types of tree or bush which are found throughout Central America and some of which are used in traditional medical applications.

The *Cecropia obtusa trecul-, Cecropia peltata, Cecropia shreberiana, Cecropia palmata, Cecropia obtusa* types in particular are found in French Guyana, the latter being the most widespread.

*Cecropia obtusa*, and other similar Cecropia types are used throughout Central America as medicinal plants.

These medicinal plants are used either in the form of external applications, particularly in the treatment of fractures, the absorption of haematomas, the healing of wounds, for disinfecting the genitalia and for pain alleviation after childbirth (see "Pharmacopées traditionnelles en Guyane: Créoles, Palikur, Wayapi" GRENAND P., MORETTI C., JAQUEMIN H., published by Orstom, 1987) or by swallowing to treat gastric or intestinal illnesses or even headaches (see BARRETT B.: "Medicinal Plants of Nicaragua's Atlantic Coast", Economic Botany, 48, 8–20, 1994/ CACERES A., and colleagues.: "Plants used in Guatemala for the treatment of gastrointestinal disorders. 1. Screening of 84 plants against enterobacteria." J. Ethnopharmacol., 30, 55–73, 1990).

Various chemical compositions in plants of the Cecropia genus emerge clearly from studies.

Therefore, the leaves contain cardenolids, flavonoids, leucoanthocyanins, triterpenes, tanins and polyphenols and the cortices contain steroids and ursolinic acid.

The presence of Ambain and Cecropin, which have cardiotonic and diuretic properties, was found in the entire plant.

In addition, the Müller-*Cecropia peltata* substances contain a polysaccharide, the structure of which appears to be close to that of glycogen and the preparation of polysaccharide from plants of the Cecropia genus has already been proposed (U.S. Pat. No. 2,871,235).

BRIEF SUMMARY OF THE INVENTION

However, the authors of the present invention have unexpectedly and surprisingly found that extracts of plants of the Cecropia genus have a certain number of advantageous properties and a very high level of tolerance which make their use in cosmetics and dermatology interesting, particularly owing to their special and pronounced action on lipolysis which make them useful in slimming preparations, but also owing to their tightening effect, their smoothing properties and the improvement of the radiance of the skin.

Therefore, the main aim of the present invention relates to the use of at least one extract of a plant of the Cecropia genus as active ingredient, alone or in combination with at least one other active ingredient, for the preparation of a product or a cosmetic or dermo-pharmaceutical composition for topical, external application for the skin, mucous membrane and/or the epithelium or body appendages (hair, nails, etc.).

DETAILED DESCRIPTION OF THE INVENTION

According to a preferred embodiment of the invention, the active ingredient can be formed by an extract of the *Cecropia obtusa* and/or *Cecropia peltata* plant(s), the parts of the plants used for the preparation of the extract or the extracts being the roots, cortices (the roots, the stalks, and the trunk), leaves and foliated stalks, fruit, grains (seeds) and/or blossoms.

The solvent used to carry out the extraction or extractions is selected from the group comprising water, alcohols, ketones, esters, ethers, polyhydric alcohols, chlorine solvents and mixtures of at least two of the aforementioned solvents.

However, the extraction can also take place with supercritical $CO_2$, alone or mixed with a secondary solvent.

According to a particular embodiment of the invention, the extract is obtained by a process which is based on wave radiation, for example microwaves or ultrasound.

According to a first alternative of the embodiment of the invention, the extract used is a total Cecropia extract which contains all active extractable components of the plant.

According to a second alternative of the embodiment of the invention, the extract is formed by a fraction which contains crude, semi-purified or purified polysaccharides.

According to a third alternative of the embodiment of the invention, the extract is formed by a fraction which contains active substances of the plant(s), with the exception of the polysaccharides.

According to an alternative of an advantageous embodiment of the invention, the extract is formed by a fraction which is at least semi-purified, for example by chromatography or a fractionated liquid/liquid or liquid/solid extraction technique.

To illustrate the invention, though without restricting its scope, various processes which can be used to carry out the extractions of plants of the Cecropia genus, which can be used directly in the sense of this invention, will now be described.

It should be noted that in the description of the following examples the part of the plants used are given as an indication, wherein the extractions, which are the subject of the invention, can be carried out using any accessible parts of the aforementioned plants.

EXAMPLE 1

Cortices of *Cecropia obtusa* trunk are crushed then mashed finely by a blade-type pulping machine.

3.75 liters of distilled water are put into a reactor with an agitator then the following operations are carried out, comprising:

adding 300 g of pulped cortex to the reactor, homogenising the now viscous solution by Ultra-Turrax, extracting with agitation for an hour while boiling (85 to 90° C.), cooling to ambient temperature, removing the insoluble materials by centrifuging at 5,000 g, collecting the materials floating on the surface from which 2.07 liters E1 extract to 1.1% of dry material are obtained, extracting the centrifuge sediment under the same operating conditions with 2.75 liters of distilled water and then proceeding as described above, to obtain 2.6 liters E2, extract to 0.71% of dry material.

The total yield of the two extractions, determined on the basis of the dry extract, is 13.7%/cortices.

The solutions obtained are then de-watered (dehydrated) by spraying or any other method known to the person skilled in the art (freeze-drying lypholisation, drying in a drying chamber etc.).

In this example, one liter E1 extract (without adding a substance) is sprayed and 7.4 g powder are obtained by this process, representing a spraying yield of 65.9%.

EXAMPLE 2

One liter of viscous extract obtained by example 1 is added with agitation to one liter of alcohol, 96°, to precipitate the polysaccharide contained therein.

The fibres formed are centrifuged and immersed at ambient temperature in 150 ml ethanol for at least one hour.

The fibres are then immersed in 200 ml acetone for one hour, centrifuged and then dried in a drying chamber aerated at 40° C.

The total weight of the polysaccharides obtained is 9.5 g, representing a theoretical yield of 6.5% cortices if the entire extract of example 1 was precipitated.

EXAMPLE 3

2.2 liters of 50% ethyl alcohol (ethanol) are put into a reactor with an agitator and then the following operations are carried out, comprising:

adding 300 g of *Cecropia obtusa* cortex pulped in the reactor according to example 1, extracting with agitation for one hour with reflux, cooling to ambient temperature, filtering the materials floating on the surface to a porosity of about 0.45 $\mu$m, collecting the brown filtrate, removing the residue (insoluble) by coarse centrifuging or filtering, evaporating the alcohol phase of the filtrate under vacuum to obtain 667 ml aqueous solution, the dissolved material content of which is 1.59% (representing an extraction yield of 3.53%/cortices), adding a malto dextrin-type substance to the solution to obtain 2/3 added substance to 1/3 extracted dry material, dewatering the solution obtained by spraying, extracting the residue with 2.25 liters of 50% ethanol under the same operating conditions and repeating the various operations as described above to obtain 875 ml of aqueous solution, the dissolved material content of which is 0.81% (representing a yield of 2.36%/cortices), spraying the solution after adding malto dextrin under the same conditions as described above.

The total theoretical yield of the extraction is 5.89%/cortices.

EXAMPLE 4

3.37 liters of distilled water are put into a reactor with an agitator and then 270 g of dried residual material (insoluble) obtained following preparation of the extract of example 3 with agitation.

The following operations are successively carried out, comprising:

agitation until soluble and then homogenisation of the now viscous mixture by Ultra-Turrax, increasing the temperature to 80 to 85° C., extracting for one hour with agitation, cooling to 30° C., centrifuging for 15 minutes at 5,000 g, collecting the brown viscous material (2 liters) floating on the surface, precipitating the polysaccharides in the extract by adding ethanol in a volume, 96°, and then proceeding as in example 2.

12.7 g polysaccharides are thus obtained, i.e. a yield of 4.70% relative to the residual material and of 4.2%/cortices.

EXAMPLE 5

2.25 liters of ethyl alcohol, 96°, are put into a reactor then the following operations are successively carried out, comprising:

adding 300 g of *Cecropia obtusa* cortex to the reactor pulped in accordance with example 1, extracting with agitation for one hour with reflux, cooling to ambient temperature, removing the undissolved material by filtering, filtering the extract obtained to a porosity of about 0.45 $\mu$m, collecting the filtrate, evaporating the solvent under vacuum at 40° C., removing the last traces of the solvent in the drying chamber at 50° C.

The weight of the extract obtained is 4.0 g, i.e. a yield of R1=1.35%/cortices.

The preparation of the residual material with 2.25 liters of alcohol under the same operating conditions allows 2.41 g of extracts to be obtained, i.e. a yield of R2=0.80%/cortices.

EXAMPLE 6

3.37 liters of distilled water are put into a reactor with blade agitator.

The following operations are then successively carried out, comprising:

adding 270 g of dried residual material (insoluble) to the extraction of the aforementioned example 5 with agitation, stirring until soluble, homogenising by Ultra-Turrax and then proceeding as in example 4.

The total weight of the mucilage obtained is 15.54 g, i.e. a yield of R1=5.75% relative to the residual material and 5.18%/cortices.

The tests for proving and evaluating the principle properties relating to the plant extracts of the Cecropia genus discovered by the inventors will now be described.

I. Evidence of the Lipolysis Activation Effect on Human Adipocytes in "in vitro" Survival The test used to emphasise the lipolysis activation of human adipocytes in the presence of Cecropia extracts, which are the subject of the present invention, is described below.

Lipolysis is removal of triglycerides (or TG) stored in the adipocytes by a hormone-sensitive enzyme, triglyceride lipase (or TGL) which splits the TG into free fatty acids and glycerin which are removed in the blood circulation. The fatty acids can then be absorbed by the muscle cells to produce energy.

1) Principle of the in vitro Test

Activation of lipolysis is evaluated by spectrophotometric metering of the rate of glycerin salted out by adipocytes, incubated "in vitro" with the substance to be tested present.

The adipocytes are isolated by enzymatic digestion of subcutaneous human tissue by the so-called Rodbell method (see M. Rodbell: "Metabolism of isolated fat cells". The journal of biological chemistry, Vol. 239, No. 2, pages 375 to 380, 1964).

2) Preparation of the Adipocytes in Suspension

The Cecropia extracts are dissolved in a defined medium which is put into contact with the adipocytes for 90 minutes at 37° C.

3) Quantisation of the Lipolysis

The rate of salted-out glycerin is quantified by spectrophotometry in the medium of the material which floats on the surface by the method described by C. Carpéné and colleagues "Discrimination des adrénergiques à potentialité α2 par l'étude de la lipolyse sur des adipocytes de hamster". (J. Pharmacol. (Paris), Vol. 12, No. 2, pages 219 to 224, 1981).

The rate of liberated glycerin is given relative to the rate of all lipids metered by turbidimetry.

The proof mass substances are theophylline and isoprenaline.

4) Results

Each extract was tested in comparison with reference substances (theophylline and isprenaline) on 2 to 5 different preparations of human adipocytes.

The results are expressed as mean values of the activation percentage relative to a proof mass batch (without Cecropia extract).

("dynamic spring rate") to be calculated. Use of a tightening product on the surface of the skin results in a DSR increase, a consequence, with constant force, of a reduction in the stretching of the skin during the stress. The tests are carried out under standardised conditions with regard to temperature and relative humidity.

2) Emphasising the Action

A patch is stuck on a 1 $cm^2$ cutaneous area of the back of the hand of a volunteer. Five measurements of the horizontal stretching are then carried out on the untreated skin as control. The placebo carrier is then applied per 10 microliters. After drying for 5 minutes five measurements serve as control for the carrier effect. The skin is then treated with the active ingredient, the tightening effect of which is measured by 5 final measurements after a further 5 minutes, waiting time. A mean measurement is taken from 5 measurements during each operation. The final results are given as a percentage variation of the DSR, on the one hand between the effect produced by water and, on the other hand, the action of the active ingredient.

3) Results

The Cecropia extracts were tested as an aqueous solution with a 1.5 concentration under these conditions using a healthy volunteer (test person).

The Cecropia extract prepared according to example 4 increases DSR by 25.4%.

The Cecropia extract prepared according to example 4 increases DSR by 52%.

The results of this test clearly show the tightening, cutaneous effect of the Cecropia extracts which can be used in cosmetic tightening products (for face and bust), reshaping products, products for the eyes and face, anti-wrinkle products and make-up products.

TABLE I

| Extract tested | Concentration | Number of tests | % activation of the lipolysis relative to the proof mass without extract (mean) |
|---|---|---|---|
| Cecropia extract prepared according to example 1 | 0.04% wt./vol. 0.08% wt./vol. | 5 5 | +41 +53 |
| Cecropia extract prepared according to example 3 | 0.05% wt./vol. 0.1% wt./vol. | 5 5 | +44 +134 |
| Cecropia extract prepared according to example 5 | 0.04% wt./vol. 0.08% wt./vol. | 5 2 | +58 +113 |
| Theophylline | 1 mM | 5 | +70 |
| Isoprenaline | 0.1 μM | 5 | +45 |

The results listed in this table show that the Cecropia extracts tested demonstrate activation of lipolysis which is close to, and in certain cases higher than, the activation observed in the presence of the control (theophylline 1 mM or isoprenaline 0.1 μM).

For this reason, the Cecropia extracts can be used in dermo-cosmetic slimming preparations allowing the triglyceride excess stored in the case of cellulitis to be reduced.

II. Evidence of a Tightening Effect by a Quantified Mass in vivo in Humans by a Horizontal Extensiometry Method 1) Principle of the Test The test consists in measuring the displacement of the skin after a constant sinusoidal force is applied parallel to its surface. It is a method of horizontal extensiometry which is carried out with a device of the type described in French Patent Application No. 98 12125 in the name of the Applicant. Processing of the force and stretching signals by an hysteresis ellipse allows the dynamic tension or DSR III. Evidence of a Softening Effect by a Quantitative in vivo Measurement in Humans by a Frictiometric Method 1) Principle of the Test The test consists in applying a constant force to the skin with a sliding block which is caused to rotate at controlled speed and controlled pressure. The moment of friction is measured. It allows the coefficient of friction of the sliding block on the skin to be measured. The coefficient of friction is dependent on the condition of the surface of the skin, particularly on its moisture content and its softness. The more hydrated and soft the skin feels, the more the coefficient of friction increases. The tests were carried out under standardised conditions with regard to temperature and relative humidity.

2) Evidence of the Action

A friction meter measurement is made on the skin without treatment (T0) on a 9 $cm^2$ cutaneous area on the antero inner side of the forearm of the volunteer. The active ingredient is then applied at a metering of 4 microliters per cm². After drying for 15 minutes a friction meter measurement serves as control for the efficacy of the active ingredient (T15). At the same time, an adjacent cutaneous area is measured as proof mass under the same conditions. The result is given in the difference in the percentage variation between T0 and T15 of the treated area relative to the area of the proof mass.

3) Results

Under these conditions the Cecropia extract prepared according to example 2 and which was tested as an aqueous solution with a 1.5% concentration on a healthy volunteer increases the coefficient of friction by 31.5%.

The result of this test demonstrates the improvement in the cutaneous softness and the moisture supplied by the Cecropia extracts.

IV. Evidence of an Action Improving the Radiance of the Complexion by a Quantitative in vivo Measurement in Humans by a Brillantometry Method 1) Principle of the Test The test consists in illuminating the skin in polarised light, then in measuring the reflected light at various angles which are equal to those of the incident light, i.e. the complete distribution of the reflected light depending on the angle. This is a goniophotometric method. The polarised light allows the viewing reflection (or the radiant reflection) to be better differentiated from the radiated reflection.

The test was carried out with the process and the device described in French Patent Application No. 98 12589 in the name of the Applicant.

The result of a measurement on the skin results in a curve of the viewing reflection according to the angle of measurement. The curve has a more or less high maximum value at 0°. The mean value of the viewing reflectivity is calculated between −60° and +60°. This mean value is representative of the radiance of the complexion. When its value increases the radiance of the complexion is improved.

The tests were carried out under standardised conditions with regard to temperature and relative humidity.

2) Evidence of the Action

A brillantometry measurement is made on the skin without treatment (T0) on a 9 cm² cutaneous area which is on the antero inner side of the forearm of the volunteer. The active ingredient is then applied at a metering of 4 microliters per cm². After drying for 5 minutes a brillantometry measurement serves as control for the efficacy of the active ingredient (T5). The result is expressed as the difference in the percentage variation between T0 and T5 on the treated cutaneous area.

3) Results

The Cecropia extracts were tested under these conditions as an aqueous solution with a 1.5% concentration on a healthy volunteer.

The Cecropia extract prepared according to example 3 increases the mean reflectivity value by 11%.

The Cecropia extract prepared according to example 6 increases the mean reflectivity value by 14%.

The results of these tests therefore prove the improving action on the radiance of the complexion by means of Cecropia extracts which can be used in cosmetic products intended for this use.

The object of the present invention also consists in a cosmetic or dermo-pharmaceutical composition for the external, topical application to the skin, characterised in that it contains as and active ingredient at least one of the slimming properties, alone or in combination with at least one other active ingredient, at least one extract of a plant of the Cecropia genus.

According to a preferred embodiment of the invention, this cosmetic or dermo-pharmaceutical composition contains as an active ingredient, which has an activating lipolysis action, tightening effects, properties for improving the radiance of the complexion and/or softening properties, at least one extract of a plant of the Cecropia genus, preferably *Cecropia obtusa* and/or *Cecropia paltata*.

The present invention also relates to a cosmetic or dermo-pharmaceutical composition for the external, topical application for the mucous membrane and/or the epithelium or body appendages (hair, nails, etc.), characterised in that it contains as a tightening active ingredient, as an active ingredient which contains an improvement in the radiance of the complexion and/or a softening active ingredient which, alone or in combination with at least one other active ingredient, at least one extract of a plant of the Cecropia genus.

According to a feature of the invention the various aforementioned cosmetic compositions advantageously contain as an active ingredient, alone or in combination with other active ingredients, between 0.001% by weight and 20% by weight, preferably between 0.1% by weight and 3% by weight of, an extract or a mixture of extracts of the plants of the Cecropia genus, particularly of *Cecropia obtusa* and/or of *Cecropia peltata*.

The extract forming the active ingredient can be used in any galenical form possible in cosmetics, for example emulsions (oil in water and water in oil), face lotions, milk, gels, hydrogels, creams, pomades, soaps, pellets, spraying materials, hair lotions and shampoos.

In addition, the extract forming the active ingredient can be added to one or more cosmetic vectors, particularly one or more vectors selected from the group comprising liposomes, macro-, micro-, or nanocapsules, macro-, micro-, or nanoparticles and other similar and known forms.

Various formulations of cosmetic compositions containing one or more extract(s) of plants of the Cecropia genus will now be described for the purpose of non-limiting illustration of possible embodiments for cosmetic products or compositions according to the invention.

EXAMPLE 1

A cosmetic product in the form of a slimming cream for the body according to the invention may, for example be of the following composition by weight, formed by the following fractions A, B and C:

| Fraction A | |
|---|---|
| glycerin stearate and Ceteareth 20 and Ceteareth 10 and ketylic palmitate | 5.0% |
| ketostearilic alcohol | 2.0% |
| decyloleate | 3.0% |
| paraffin oil | 3.0% |
| karite butter | 3.0% |
| Fraction B | |
| glycerin | 3.0% |
| hydrolysed wheat proteins | 0.5% |
| Cecropia ethanolic extracts according to Example 5 of the process | 2.0% |
| water | 78.3% |
| Fraction C | |
| Perfume | 0.2% |

The preparation procedure consists in the separate preparation of fractions A and B while stirring at 80° C., in adding fraction A to fraction B with turbine agitation, then in cooling the mixture to ambient temperature and lastly in adding fraction C.

EXAMPLE 2

A cosmetic product in the form of a slimming gel for the body according to the invention may, for example be of the composition by weight, formed by the following fractions A, B, C, D, E and F:

| Fraction A | |
|---|---|
| distilled water | 49.95% |
| Elastab 50J (Laboratoires Sérobiologiques) | 0.5% |
| carrageenan | 0.1% |
| Fraction B | |
| carbomer | 0.35% |
| distilled water | 31.95% |
| Fraction C | |
| propylene glycol | 2.00% |
| dimethicon copolyol | 3.00% |
| Fraction D | |
| 20% triethanolamine in aqueous solution | 2.1% |
| Fraction E | |
| Kathon CG (from Rohm and Haas) | 0.05% |
| Fraction F | |
| 50% Cecropia ethanol extract according to example 3 of the process | 1.0% |
| distilled water | 9.0% |

The preparation procedure of the aforementioned gel consists primarily in the separate preparation of fractions A and B at 75° C. with turbine agitation, then in its cooling to ambient temperature and then in the preparation of fraction F by dispersing the extract in ten times its weight of water and in gradually adding the fractions B, C, D, E and F at ambient temperature and with turbine agitation and lastly in continuing planetary agitation until homogenised.

The invention is of course not restricted to the embodiments described. Modifications are possible, particularly in the composition of the various elements or through replacement by industrial equivalents, without thereby going beyond the scope of the invention.

What is claimed is:

1. A method of producing a cosmetic or pharmaceutical preparation with an activating effect of lipolysis on skin, mucous membrane, epithelium or body appendages on an individual, comprising:

adding at least one extract of a plant belonging to the Cecropia genus to a cosmetic and/or dermopharmaceutical preparation, wherein said extract is added in an amount of 0.001% to 20% by weight of the preparation.

2. The method according to claim 1, wherein said extract is an ethanol extract formed from *Cecropia obtusa* cortices.

3. The method according to claim 1, wherein said extract is an alcohol extract formed from *Cecropia obtusa* cortices.

4. The method according to claim 1 wherein said extract is obtained with a solvent selected from the group consisting of water, alcohols, ketones, esters, ethers, polyhydric alcohols, chlorine solvents, and combinations thereof and formed from parts of said Cecropia plant selected from the group consisting of roots, cortices, leaves, foliated stalks, fruit, grains and blossoms.

5. The method according to claim 1, wherein said extract is obtained with a supercritical $CO_2$ solvent.

6. The method according to claim 1, wherein said extract is obtained by a process based on wave radiation.

7. The method according to claim 1, wherein said extract is formed from plant parts selected from the group consisting of roots, cortices, leaves, foliated stalks, blossoms, fruit and grains.

8. The method according to claim 1, wherein said extract is formed from a fraction which contains crude, semi-purified or purified polysaccharides.

9. The method according to claim 1, wherein said extract is used in quantities between 0.1%–3% by weight based on said preparation.

10. The method according to claim 1, wherein said extract is incorporated in one or more vectors selected from the group consisting of liposomes, macro-, micro- or nanoparticles and other similar forms.

11. A method of applying in an individual a cosmetic or pharmaceutical preparation to create an activating effect of lipolysis on skin, mucous membrane, epithelium or body appendages, comprising:

applying said preparation on said individual's skin, mucous membrane, and/or epithelium or body appendages, wherein said preparation contains at least one extract of a plant belonging to the Cecropia genus in an amount of 0.001% to 20% by weight of the preparation, and wherein said extract has an activating effect of lipolysis on skin, mucous membrane and/or epithelium or body appendages.

12. The method according to claim 11, wherein said extract is an ethanol extract formed from *Cecropia obtusa* cortices.

13. The method according to claim 11, wherein said preparation is applied to said individual as an active ingredient with slimming properties.

14. The method according to claim 11, wherein said preparation is applied to said individual as a tightening active ingredient.

15. The method according to claim 11, wherein said preparation is applied to said individual as an active ingredient for improving the radiance of a complexion.

16. The method according to claim 11, wherein said preparation is applied to said individual as a softening active ingredient.

17. The method according to claim 11, wherein said extract is an alcohol extract formed from *Cecropia obtusa* cortices.

18. The method according to claim 11, wherein said extract is obtained with a solvent selected from the group consisting of water, alcohols, ketones, esters, ethers, polyhydric alcohols, chlorine solvents, and combinations thereof and formed from plants selected the group consisting of *Cecropia obtusa* and *Cecropia peltata*.

19. The method according to claim 11, wherein said extract has been obtained by a process based on wave radiation or with a solvent selected from the group consisting of water, alcohols, ketones, esters, ethers, polyhydric alcohols, chlorine solvents, combinations thereof and supercritical CO2, and wherein said extract is formed from plants selected from the group consisting of *Cecropia obtusa* and *Cecropia peltata*.

20. A method of applying in an individual a cosmetic or pharmaceutical preparation with an activating effect of lipolysis on skin, mucous membrane, epithelium or body appendages, comprising:

applying said preparation on said individual's skin, mucous membrane, and/or epithelium or body appendages, wherein said preparation contains at least one extract of a plant belonging to the Cecropia genus, wherein said extract has an activating effect of lipolysis on skin, mucous membrane and/or epithelium or body appendages, wherein said extract has been obtained by a process based on wave radiation or with a solvent selected from the group consisting of water, alcohols, ketones, esters, ethers, polyhydric alcohols, chlorine solvents, combinations thereof and supercritical CO2, and wherein said extract is formed from parts of said Cecropia plant selected from the group consisting of roots, cortices, leaves, foliated stalks, fruit, grains and blossoms.

* * * * *